United States Patent [19]

Matthewson

[11] 4,404,223
[45] Sep. 13, 1983

[54] PESTICIDAL FORMULATIONS

[75] Inventor: Michael D. Matthewson, Berkhamsted, England

[73] Assignee: Burroughs Wellcome Co., Raleigh, N.C.

[21] Appl. No.: 251,101

[22] Filed: Apr. 6, 1981

Related U.S. Application Data

[63] Continuation of Ser. No. 43,491, May 29, 1979, abandoned.

[30] Foreign Application Priority Data

May 30, 1978 [GB] United Kingdom ............... 24264/78
May 30, 1978 [GB] United Kingdom ............... 24265/78

[51] Int. Cl.$^3$ ..................... A01N 37/34; A01N 37/00; A01N 37/08
[52] U.S. Cl. ..................... 424/304; 424/305
[58] Field of Search ......................... 424/304

[56] References Cited

U.S. PATENT DOCUMENTS

| | | | |
|---|---|---|---|
| 3,702,891 | 11/1972 | Hamuro | 424/285 |
| 3,723,615 | 3/1973 | Okuno | 424/306 |
| 3,899,586 | 8/1975 | Okuno et al. | 424/40 |
| 3,906,089 | 9/1975 | Okuno et al. | 424/45 |
| 3,934,023 | 1/1976 | Okuno et al. | 424/306 |
| 4,100,297 | 7/1978 | Grandadam et al. | 424/306 |

FOREIGN PATENT DOCUMENTS

| | | | |
|---|---|---|---|
| 116329 | 7/1967 | Denmark | 424/306 |
| 51-32728 | 3/1976 | Japan | 424/306 |

Primary Examiner—Douglas W. Robinson
Attorney, Agent, or Firm—Donald Brown

[57] ABSTRACT

Pyrethroid esters of the formula (I)

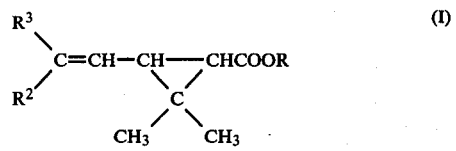

potentiate the activity of each other against arthropod pests. Values of $R^2$ and $R^3$ include halogen and R includes phenoxybenzyl and α-cyanophenoxybenzyl. Compositions comprise of two or more esters of (I) and formulations comprise such compositions in association with a carrier. The esters (I) are used to combat arthropods.

4 Claims, No Drawings

PESTICIDAL FORMULATIONS

This is a continuation of application Ser. No. 043,491, filed May 29, 1979, now abandoned.

This invention relates to novel potentiating compositions, their preparation, formulations containing them, the preparation of such formulations and to their use for the control of arthropod pests.

Arthropod pests are troublesome to man, animals and plants. They are vectors of disease, and economic losses result from their depredations on plants and animals. Control of such pests over the years has come to depend strongly upon the use of chemical pesticides, and prominent amongst those which have been extensively investigated are pyrethroids-esters of cyclopropane carboxylic acid derivatives.

Amongst pyrethroids known to be active against a variety of arthropod pests are the compounds of formula (I). These are disclosed in British Patent Specifications, Nos. 1,413,491, 1,448,228, 2000 764A and include a number of compounds having considerable potency as insecticides.

It has now been found that the activity against arthropod pests of one compound of formula (I) can be potentiated by another compound of formula (I). For example, the ixodicidal activities of the compounds 3-phenoxybenzyl (±)-cis, trans-2,2-dimethyl-3-(2,2-dichlorovinyl)cyclopropane-1-carboxylate (permethrin) and (−)-α-cyano-3-phenoxybenzyl (+)-cis-2,2-dimethyl-3-(2,2-dibromovinyl)cyclopropane-1-carboxylate (decamethrin) are potentiated by mixtures of these compounds when tested against the cattle tick *Boophilus microplus*.

In the compounds of formula (I):

$$\begin{array}{c} R^3 \\ \diagdown \\ R^2 \diagup \end{array} C=CH-CH-\!\!\!\!-\!\!\!\!-CHCOOR \quad (I)$$
$$\begin{array}{c} \diagdown \diagup \\ C \\ \diagup \diagdown \\ CH_3 \quad CH_3 \end{array}$$

$R^2$ represents halo and $R^3$ represents alkyl or halo; R represents a group of the formula:

(III)

(IV)

(V)

(VI)

(VIA)

(VIB)

wherein
Z represents O, S, $CH_2$ or CO, Y represents hydrogen, alkyl, alkenyl or alkynyl, or aryl or furyl which is unsubstituted or substituted in the ring by one or more alkyl, alkenyl, alkoxy or halo radicals.
$R^7$ and $R^8$, which may be the same or different, each represent hydrogen, alkyl or alkenyl,
$R^9$ represents hydrogen or methyl,
$R^{10}$ and $R^{11}$, which may be the same or different, each represent hydrogen or alkyl,
$R^{12}$ represents an organic radical having carbon-carbon unsaturation in a position α to the $CH_2$ group to which $R^{12}$ is attached, indicates an aromatic ring or a dihydro or tetrahydro analogue thereof,
$X^1$, $X^2$, $X^3$ and $X^4$, which may be the same or different, each represent hydrogen, chloro or methyl,
$Z^3$ represents —$CH_2$— or —O— or —S— or —CO—,
D represents hydrogen, cyano or —C≡CH,
$Z^1$ and $Z^2$, which may be the same or different, each represent chloro or methyl, and
each n, which may be the same or different, is 0, 1 or 2;
or when R is a phenoxybenzyl group optionally substituted in the α- position by ethynyl or cyano, $R^3$ may also be a haloalkyl group having 1 or 2 carbon atoms, when $R^2$ is halo.

Formula (I) is intended to encompass all the possible geometric and optical isomers. More particularly the acid moiety of the ester may be selected from the (+)-cis-isomer, the (+)-trans-isomer, the (±)-cis-isomer, the (±)-trans-isomer and the (±)-cis,trans-isomer (the stereochemistry referring to that of the cyclopropane ring), and especially from the dihalo acids such as the dichloro and dibromo acids (in formula (I) $R^2$, $R^3$=Cl or Br). The alcohol moiety may especially be chosen from 3-phenoxybenzyl alcohol and α-cyano-3-phenoxybenzyl alcohol. Preferred esters of formula (I) which may be used together include permethrin; decamethrin; (±)-α-cyano-3-phenoxybenzyl-(±)-cis,trans-2,2-dimethyl-3-(2,2-dichlorovinyl)cyclopropane-1-carboxylate (cypermethrin); (±)-α-cyano-3-phenoxybenzyl-(+)-cis-2,2-dimethyl-3-(2,2-dibromovinyl)cyclopropane-1-carboxylate; α-cyano-3-phenoxybenzyl 3-(2-chloro-3,3,3-trifluoroprop-1-emyl)-2,2-dimethylcyclopropane-1-carboxylate.

Two or more compounds of formula (I) may therefore be used together to control arthropod pests and especially insects and acarines. Insects and acarines requiring control for agricultural, public health, domestic, veterinary and medical purposes include adult and juvenile stages of flies, mites, ticks, cockroaches, mosquitoes, tsetse fly, moths including warehouse and clothes moths, fleas, lice, and timber and grain infesting insects and other ectoparasites of mammals and birds.

The compounds may be used to combat arthropod infestations either as a mixture of the raw chemicals (hereafter called the 'compositions') or as a formulation with an inert carrier or diluent. The formulations may be prepared by customary methods as dusts or granular solids, wettable powders, pyrotechnic or vaporising formulations including mosquito coils and vaporising mats, baits, solutions, laquers, creams, pastes, gels, foams, greases, shampoos, ointments, emulsifiable concentrates, sprays, aerosols and other liquid preparations after the addition of appropriate solvents, synergists, diluents and surface active agents. The formulations may contain up to 99% by weight of a mixture of compounds of formula (I) and may be diluted prior to use.

Such formulations may be applied directly to arthropod pests or to their environment by dusting, spraying, pouring, fogging, vaporisation, painting and other methods customarily used in arthropod control. The amount and concentration of a mixture of compounds of formula (I) which should be applied will vary with the nature of the compounds and formulation, the pests to be controlled, and the habitat and method of application but in general the total concentration should be in the range of 0.0001 to 1.0% w/v. In a composition, the compounds of formula (I) should be present in potentiating amounts from 200/1 to 1/200 especially 10/1 to 1/10, parts by weight of the repective compounds.

Accordingly there is provided by the present invention the following aspects:

(a) A novel composition comprising a mixture of two or more esters of formula (I);

(b) A pesticidal formulation comprising a composition as defined in paragraph (a) together with a carrier therefor;

(c) A method of producing such a formulation; and (d) A composition or a formulation as defined in paragraphs (a) or (b) for use as a pesticide.

The following Examples are provided by way of an illustration of the present invention and should not be construed as in any way constituting a limitation thereof.

EXAMPLE 1

Engorged female ticks of the biarra strain of *Boophilus microplus* are immersed, in groups of 20 ticks per concentration, in a range of dilutions of (−)-α-cyano-3-phenoxybenzyl-(+)-cis-2,2-dimethyl-3-(2,2-dibromovinyl)cyclopropane-1-carboxylate (hereafter referred to as decamethrin) in combination with 3-phenoxybenzyl (±)-cis,trans-2,2-dimethyl-3-(2,2-dichlorovinyl)cyclopropane-1-carboxylate (hereinafter referred to as premethrin) at a ratio of 1/1 w/w of decamethrin and permethrin.

The composite wash is prepared by mixing the two constituents at a ratio of 1:1 and then diluting the mixture with water to give the desired range of concentration for the test. The constituents were in the form of miscible oil concentrates.

The ticks are removed from the wash after 10 minutes, dried, and stuck dorsal side down on double-sided adhesive tape. They remain in this position for 14 days when the numbers laying viable eggs are determined. From this data a regression line is plotted (concentration against % inhibition of egg-production) and the IR99 values determined (Table 1).

IR99 = concentration at which 99% inhibition of egg-production occurs.

The values so obtained for the composite wash are compared with similar values obtained for the constituents of the composite wash when alone. By reference to the equation for the harmonic mean, the factor of potentiation is determined (Table 1).

The equation for the harmonic mean is:

$$X = \frac{\text{Proportion of } A + \text{Proportion of } B}{\frac{\text{Proportion of } A}{\text{IR99 } A} + \frac{\text{Proportion of } B}{\text{IR99 } B}}$$

$$Y = \frac{X}{\text{IR99 mixture of } A \text{ and } B}$$

Factor of Potentiation (FOP) =

$$\frac{Y \times \text{Proportion of } A}{\text{Proportion of } A + \text{Proportion of } B}$$

TABLE 1

| Chemical | B. microplus Biarra strain | |
|---|---|---|
| | IR99 (%) | Factor of Potentiation |
| Permethrin | 0.13 | — |
| Decamethrin | 0.0039 | — |
| Permethrin/Decametrin (1:1) | 0.00032 | 11.9 |

EXAMPLE 2-Wettable Powders

| | (a) | (b) |
|---|---|---|
| PERMETHRIN | 2.5 | 15.0 part by weight |
| DECAMETHRIN | 2.5 | 15.0 part by weight |
| FINE SILICA | 5.0 | 20.0 part by weight |
| KAOLIN | 84.5 | 44.5 part by weight |
| SODIUM ALKYL NAPHTHALENE SULPHONATE | 0.5 | 0.5 part by weight |
| SODIUM SALT OF CONDENSED NAPHTHALENE SULPHONIC ACID | 5.0 | 5.0 part by weight |
| | 100.0 | 100.0 part by weight |

EXAMPLE 3-Miscible Oils

| PERMETHRIN | 2.5 | 12.5 part by weight |
|---|---|---|
| DECAMETHRIN | 2.5 | 12.5 part by weight |
| SOLVENT 200 | 82.5 | 57.5 part by weight |
| CYCLOHEXANONE | — | 5.0 part by weight |
| ETHYLAN KEO | 8.5 | 7.5 part by weight |
| TERGITOL XD | 0.7 | 1.5 part by weight |
| ARYLAN CA | 3.3 | 3.5 part by weight |
| | 100.0 | 100.0 part by weight |

'Solvent 200' is a liquid comprising 95% aromatic hydrocarbons. 'Ethylan KEO' is an emulsifying agent of a nonyl phenol ethoxylate condensate with ethylene oxide having an average chain length of 9.5 mols. 'Tergitol XD' is a non-ionic liquid emulsifier of a polyalkylene glycol ether. 'Arylane CA' is an emulsifier of calcium dodecyl benzene sulphonate.

EXAMPLE 4-Dusts

| PERMETHRIN | 0.01 | 1.0 part by weight |
|---|---|---|
| DECAMETHRIN | 0.01 | 1.0 part by weight |
| TALC | 99.98 | 98.0 part by weight |
| | 100.00 | 100.0 part by weight |

EXAMPLE 5

The potentiation of permethrin and decamethrin against the house fly, *Musca domestica,* was determined. The $LD_{50}$ of the individual compounds permethrin and Decametrin were separately determined, and the pyrethroids applied in combination in ratios approximately equal to the ratios of their $LD_{50}$. The compounds were applied topically in a solution of cellosolve by a microapplicator.

Using regression lines, the median lethal doses were determined and the theoretical $LD_{50}$ found by harmonic mean calculation to give the following results:

| | $LD_{50}$ (experimental) | $LD_{50}$ (theoretical) | Factor of potentiation |
|---|---|---|---|
| Permethrin | 0.023 | — | — |
| Decamethrin | 0.007 | — | — |
| Permethrin: Decamethrin (50:1) | 0.0027 | 0.014 | 5.2 |

What we claim is:

1. A pesticidal composition comprising the esters permethrin and decamethrin, each ester present in an amount to potentiate the other in a ratio of between 1:1 to 50:1 by weight respectively.

2. The method of killing ticks or flies which comprises contacting ticks or flies with a pesticidally effective amount of the composition of claim 1.

3. A pesticidal composition comprising permethrin and decamethrin which are present in the ratio of 1 part each by weight.

4. The method of killing ticks or flies which comprises contacting ticks or flies with a pesticidally effective amount of the composition of claim 3.

* * * * *